US00PP30378P3

(12) United States Plant Patent
Holtmaat

(10) Patent No.: US PP30,378 P3
(45) Date of Patent: Apr. 9, 2019

(54) ***ECHINACEA* PLANT NAMED 'DROP352'**

(50) Latin Name: *Echinacea purpurea*
Varietal Denomination: Drop352

(71) Applicant: Henricus Maria Joseph Holtmaat, Zuidwolde (NL)

(72) Inventor: Henricus Maria Joseph Holtmaat, Zuidwolde (NL)

(73) Assignee: AB Kwekersrechten B.V., Zuidwolde (NL)

( * ) Notice: Subject to any disclaimer, the term of this patent is extended or adjusted under 35 U.S.C. 154(b) by 0 days.

(21) Appl. No.: 15/731,579

(22) Filed: Jul. 3, 2017

(65) Prior Publication Data

US 2019/0008083 P1 Jan. 3, 2019

(51) Int. Cl.
*A01H 5/02* (2018.01)
*A01H 6/14* (2018.01)

(52) U.S. Cl.
USPC ..... Plt./428
CPC ..... *A01H 6/1448* (2018.05)

(58) Field of Classification Search
USPC ..... Plt./428
CPC . A01H 5/025; A01H 5/02; A01H 5/00; A01H 6/14; A01H 6/1448
See application file for complete search history.

(56) References Cited

PUBLICATIONS

American Nurseryman New Plants 2017: Garden World Inc. (Dec. 16, 2016), retrieved on May 17, 2018, retrieved from the Internet at https://www.amerinursery.com/plants/new-plants-2017-garden-world-inc/, 4 pp. (Year: 2016).*

* cited by examiner

*Primary Examiner* — June Hwu
(74) *Attorney, Agent, or Firm* — C. A. Whealy

(57) ABSTRACT

A new and distinct cultivar of *Echinacea* plant named 'Drop352', characterized by its broadly upright plant habit; moderately vigorous growth habit; freely branching habit; strong flowering stems; numerous large double-type inflorescences with orange yellow-colored ray florets that become yellow green with development and bright yellow-colored disc florets; and good garden performance.

2 Drawing Sheets

Botanical designation: *Echinacea purpurea.*
Cultivar denomination: 'DROP352'.

BACKGROUND OF THE INVENTION

The present invention relates to a new and distinct cultivar of *Echinacea* plant, botanically known as *Echinacea purpurea*, and hereinafter referred to by the name 'Drop352'.

The new *Echinacea* plant is a product of a planned breeding program conducted by the Inventor in Zuidwolde, The Netherlands. The objective of the breeding program is to develop new freely branching and relatively compact *Echinacea* plants with unique and attractive ray floret coloration.

The new *Echinacea* plant originated from an open-pollination in July, 2014 in Zuidwolde, The Netherlands of *Echinacea purpurea* 'Meringue', disclosed in U.S. Plant Pat. No. 20,537, as the female, or seed, parent with an unknown selection of *Echinacea purpurea* as the male, or pollen, parent. The new *Echinacea* plant was discovered and selected by the Inventor as a single flowering plant from within the progeny of the stated open-pollination grown in a controlled greenhouse environment in Zuidwolde, The Netherlands in July, 2015.

Asexual reproduction of the new *Echinacea* plant by in vitro meristem culture in a controlled environment in Zuidwolde, The Netherlands since June, 2016 has shown that the unique features of this new *Echinacea* plant are stable and reproduced true to type in successive generations.

SUMMARY OF THE INVENTION

Plants of the new *Echinacea* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Drop352'. These characteristics in combination distinguish 'Drop352' as a new and distinct *Echinacea* plant:

1. Broadly upright plant habit.
2. Moderately vigorous growth habit.
3. Freely branching habit.
4. Strong flowering stems.
5. Numerous large double-type inflorescences with orange yellow-colored ray florets that become yellow green with development and bright yellow-colored disc florets.
6. Good garden performance.

Plants of the new *Echinacea* can be compared to plants of the female parent, 'Meringue'. Plants of the new *Echinacea* differ primarily from plants of 'Meringue' in the following characteristics:

1. Flowering stems of plants of the new *Echinacea* are longer than flowering stems of plants of 'Meringue'.
2. Plants of the new *Echinacea* have smaller inflorescences than plants of 'Meringue'.

Plants of the new *Echinacea* can be compared to plants of *Echinacea hybrida* 'Meteor Yellow', disclosed in U.S. Plant Pat. No. 25,149. In side-by-side comparisons, plants of the new *Echinacea* differ primarily from plants of 'Meteor Yellow' in the following characteristics:

1. Plants of the new *Echinacea* are shorter than plants of 'Meteor Yellow'.
2. Flowering stems of plants of the new *Echinacea* are not as strong as flowering stems of plants of 'Meteor Yellow'.
3. Plants of the new *Echinacea* are more freely flowering than plants of 'Meteor Yellow'.

BRIEF DESCRIPTION OF THE PHOTOGRAPHS

The accompanying photographs illustrate the overall appearance of the new *Echinacea* plant showing the colors as true as it is reasonably possible to obtain in colored reproductions of this type. Colors in the photographs may differ slightly from the color values cited in the detailed botanical description which accurately describe the colors of the new *Echinacea* plant.

The photograph on the first sheet is a side perspective view of a typical flowering plant of 'Drop352' grown in a container.

The photographs on the second sheet are close-up views of typical inflorescences (upper photograph) and the upper surface of a typical leaf (lower photograph) of 'Drop352'.

DETAILED BOTANICAL DESCRIPTION

The aforementioned photographs and following observations and measurements describe plants grown during the summer in 19-cm containers in an outdoor nursery in Zuidwolde, The Netherlands and under cultural practices typically used in commercial *Echinacea* production. During the production of the plants, day temperatures ranged from 18° C. to 30° C. and night temperatures ranged from 6° C. to 18° C. Plants were six months old when the photographs and description were taken. In the following description, color references are made to The Royal Horticultural Society Colour Chart, 2015 Edition, except where general terms of ordinary dictionary significance are used.

Botanical classification: *Echinacea purpurea* 'Drop352'.

Parentage:

*Female parent*.—*Echinacea purpurea* 'Meringue', disclosed in U.S. Plant Pat. No. 20,537.

*Male parent*.—Unknown selection of *Echinacea purpurea*, not patented.

Propagation:

*Type*.—By in vitro meristem culture.

*Time to initiate roots, summer*.—About one week at temperatures about 25° C.

*Time to produce a rooted young plant, summer*.—About five weeks at temperatures about 21° C.

*Root description*.—Fine, fibrous; typically pale cream in color, actual color of the roots is dependent on substrate composition, water quality, fertilizer type and formulation, substrate temperature and physiological age of roots.

*Rooting habit*.—Freely branching; dense.

Plant description:

*Plant form and growth habit*.—Herbaceous perennial; broadly upright plant habit, narrow inverted triangle; freely branching habit with about seven lateral branches developing per plant; moderately vigorous growth habit; moderate growth rate.

*Plant height, soil level to top of foliar plane*.—About 31.5 cm.

*Plant height, soil level to top of floral plane*.—About 47.6 cm.

*Plant diameter or spread*.—About 43 cm.

*Lateral branches*.—Length: About 17.4 cm. Diameter: About 4 mm. Internode length: About 4.6 cm. Aspect: About 40° from vertical. Strength: Moderately strong. Texture and luster: Densely pubescent; moderately glossy. Color: Close to 144A to 144B.

Leaf description:

*Basal leaves*.—Arrangement: Alternate, simple. Length: About 12.4 cm. Width: About 5.6 cm. Shape: Ovate. Apex: Acute. Base: Attenuate to short attenuate. Margin: Entire to shallowly dentate. Texture and luster, upper and lower surfaces: Moderately pubescent, strigose, rough, slightly rugose; matte. Venation pattern: Pinnate. Color: Developing leaves, upper and lower surfaces: Close to 143B. Fully expanded leaves, upper surface: Close to NN137B; venation, close to 144A to 144B. Fully expanded leaves, lower surface: Close to 147B; venation, close to 145A to 145B. Petioles, basal leaves: Length: About 7.6 cm. Width: About 2.5 mm. Height: About 2.5 mm. Strength: Strong, flexible. Texture and luster, upper and lower surfaces: Sparsely pubescent; glossy. Color, upper surface: Close to 144A. Color, lower surface: Close to 144B.

*Cauline leaves*.—Arrangement: Alternate, simple. Length: About 9.9 cm. Width: About 3.5 cm. Shape: Ovate. Apex: Acute. Base: Attenuate to short attenuate. Margin: Entire to shallowly dentate. Texture and luster, upper and lower surfaces: Moderately pubescent, strigose; matte. Venation pattern: Pinnate. Color: Developing leaves, upper and lower surfaces: Close to 143B. Fully expanded leaves, upper surface: Close to NN137B; venation, close to 144A and 144B. Fully expanded leaves, lower surface: Close to 147B; venation, close to 145A to 145B. Petioles, cauline leaves: Length: About 1.9 cm. Width: About 2 mm. Height: About 2 mm. Strength: Strong, flexible. Texture and luster, upper and lower surfaces: Sparsely pubescent; glossy. Color, upper surface: Close to 144A. Color, lower surface: Close to 144B.

Inflorescence description:

*Appearance*.—Large double-type inflorescences with ray and disc florets arranged on a capitulum; inflorescences positioned upright above the foliar plane on strong peduncles.

*Flowering habit*.—Freely flowering habit with about 14 inflorescences per plant during the flowering season.

*Fragrance*.—Slightly fragrant, slightly acidic and pleasant.

*Time to flower*.—Plants begin flowering about 100 days after planting; in the garden, plants flower continuously during the summer in The Netherlands.

*Inflorescence longevity*.—Inflorescences maintain good substance for about two weeks on the plant; inflorescences not persistent.

*Inflorescence buds*.—Height: About 1.8 cm. Diameter: About 2.7 cm. Shape: Flattened globular. Texture and luster: Smooth, glabrous; matte. Color: Close to 144A to 144B.

*Inflorescence size*.—Diameter: About 5.2 cm. Depth (height): About 6.2 cm. Disc diameter: About 5.1 cm.

*Receptacles*.—Height: About 1.1 cm. Diameter: About 8 mm. Color: Close to NN155A.

*Ray florets*.—Quantity and arrangement: About 14 arranged in a single whorl. Length: About 4.1 cm. Width: About 1 cm. Shape: Oblanceolate; mostly straight. Apex: Moderately emarginate. Base: Cuneate. Margin: Entire. Texture and luster, upper surface: Smooth, glabrous, moderately velvety; slightly glossy. Texture and luster, lower surface: Smooth, glabrous, slightly velvety; moderately glossy. Aspect: Drooping, about 60° below horizontal. Color: When opening, upper surface: Close to 21A. When opening, lower surface: Close to 20C. Fully opened, upper surface: Close to 150D; venation, close to 150D; color does not fade with development. Fully opened, lower surface: Close to 154D; apex, close to 145B; venation, close to 154D; color does not fade with development.

*Disc florets*.—Quantity and arrangement: About 240 per inflorescence, arranged spirally at the center of the receptacle. Length: About 2.1 cm. Diameter: About 5 mm. Shape: Obovate. Apex: Emarginate. Base: Cuneate. Margin: Entire. Aspect: Upright to outwardly. Texture and luster, inner and outer surfaces: Smooth, glabrous; glossy. Color: When opening, upper surface: Close to 21B. When opening, lower surface: Close to 22C. Fully opened, upper surface: Close to 11A; towards the apex, close to 8B; venation, close to 11A and 8B; color does not fade with development. Fully opened, lower surface: Close to 11B; venation, close to 11B; color does not fade with development.

*Receptacle spines*.—Quantity: One per disc floret. Length: About 1.1 cm. Diameter: About 1 mm. Shape: Acicular. Apex: Narrowly acute. Base: Cuneate. Texture and luster: Smooth, glabrous; glossy. Color: Apex: Close to 17B. Mid-section: Close to 144C to 144D. Base: Close to 145D.

*Involucral bracts*.—Quantity per inflorescence: About 40 arranged in about two whorls. Length: About 1.1 cm. Width: About 2 mm. Shape: Narrowly ovate. Apex: Acute. Base: Cuneate. Margin: Entire; moderately pubescent. Texture and luster, upper and lower surfaces: Smooth, glabrous; slightly glossy. Color, upper surface: Close to 137B. Color, lower surface: Close to 137D.

*Peduncles*.—Length, terminal peduncle: About 11.6 cm. Diameter, terminal peduncle: About 2.5 mm. Strength: Strong. Aspect, terminal peduncle: Upright. Texture and luster: Moderately pubescent; moderately glossy. Color: Close to 144B.

*Reproductive organs*.—Androecium: Not observed on ray or disc florets. Gynoecium (present only on disc florets): Quantity per floret: One. Pistil length: About 5.5 mm. Style length: About 4.5 mm. Style color: Close to 145C. Stigma diameter: About 2 mm. Stigma shape: Decurrent, cleft. Stigma color: Close to 13A. Ovary color: Close to 145D. Seeds and fruits: Seed and fruit development have not been observed on plants of the new *Echinacea* to date.

Disease & pest resistance: Plants of the new *Echinacea* have not been shown to be resistant to pathogens and pests common to *Echinacea* plants.

Garden performance: Plants of the new *Echinacea* have exhibited good garden performance and to tolerate rain and wind. Plants of the new *Echinacea* have been observed to tolerate high temperatures of about 35° C. and to be suitable for USDA Hardiness Zones 3 to 10.

It is claimed:

1. A new and distinct *Echinacea* plant named 'Drop352' as illustrated and described.

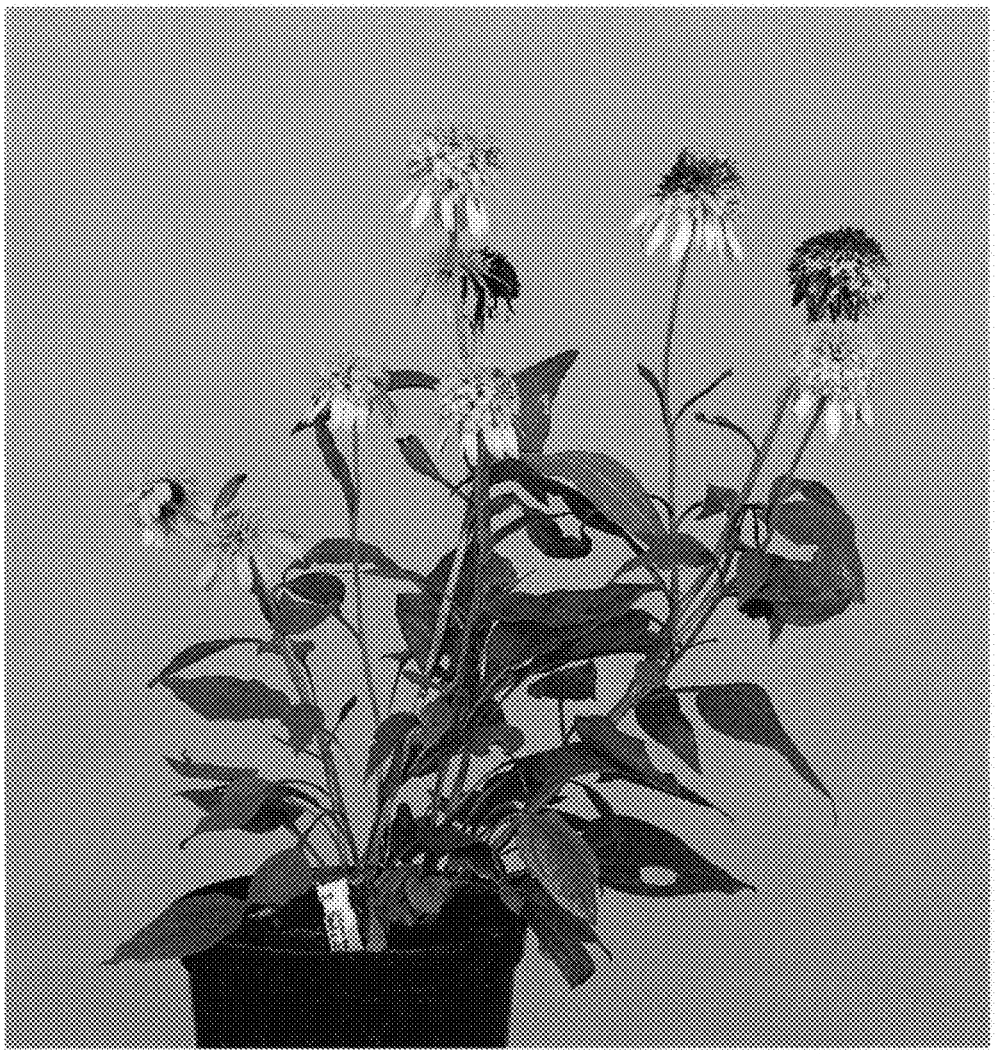

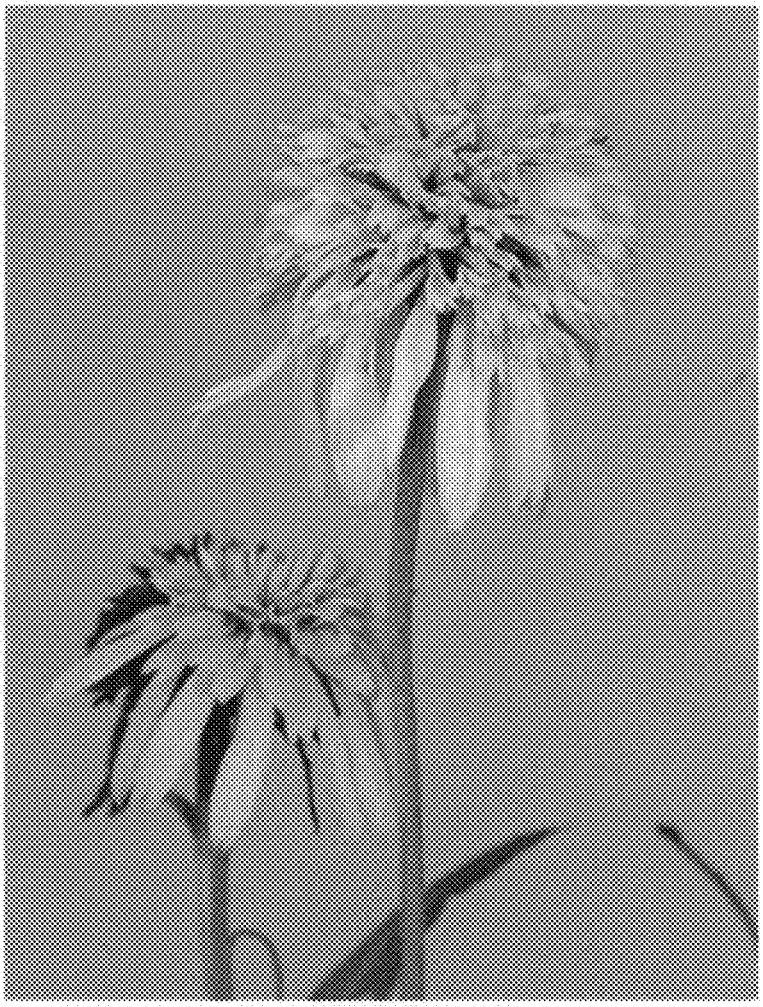
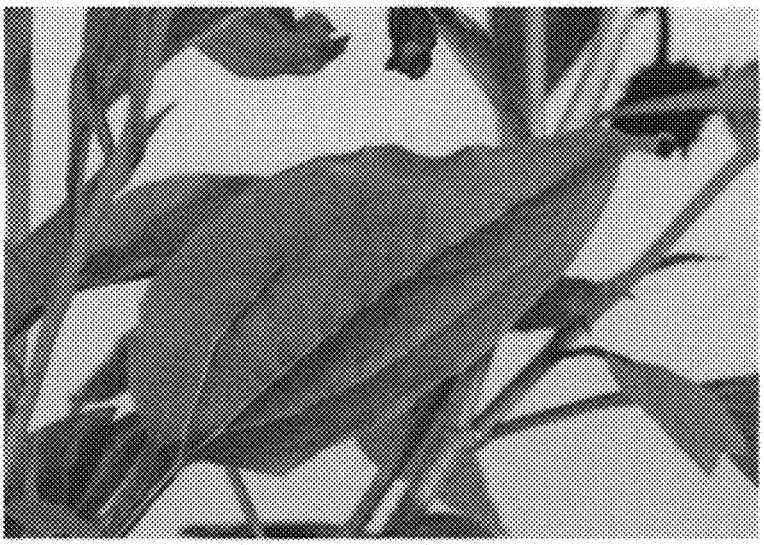

* * * * *